United States Patent [19]

Drees et al.

[11] 4,079,133

[45] Mar. 14, 1978

[54] SAFER METHOD FOR DISSOLVING GALLSTONES COMBINING HYODEOXYCHOLIC ACID WITH CHENODEOXYCHOLIC ACIDS

[75] Inventors: David T. Drees, Columbus, Ohio; Anthony R. Imondi, Doylestown, Pa.

[73] Assignee: Warren-Teed Laboratories, Inc., Wilmington, Del.

[21] Appl. No.: 655,927

[22] Filed: Feb. 6, 1976

[51] Int. Cl.² ............................................. A61K 31/56
[52] U.S. Cl. ...................................... 424/239; 424/238
[58] Field of Search ................ 424/238, 239, 316, 317

[56] References Cited
PUBLICATIONS

Thistle, NEJ Med., vol. 289, No. 13, Sep. 27, 1973, pp. 655–659.

Goldstein, J. Lab & Clin. Med., vol. 85, No. 6, Jun., 1975 pp. 1032–1040.
Matsumoto, Chem. Abs. vol. 83, Sep. 29, 1975, Ab. No. 112022d.
Matumoto, Chem. Abs. vol. 81, 1974 Ab. No. 130965b.
Wheeler, Chem. Abs. vol. 79, 1973 Ab. No. 40718c.
Dam, Chem. Abs. vol. 78, 1973 Ab. No. 695r.

*Primary Examiner*—Albert T. Meyers
*Assistant Examiner*—A. P. Fagelson
*Attorney, Agent, or Firm*—Marion C. Staves

[57] ABSTRACT

The administration of hyodeoxycholic acid (HDCA) with chenodeoxycholic acid (CDCA) effects a lowering of serum glutamic-oxaloacetic transaminase, serum glutamic-pyruvate transaminase and alkaline phosphatase in the blood relative to the administration of CDCA alone.

4 Claims, No Drawings

SAFER METHOD FOR DISSOLVING GALLSTONES COMBINING HYODEOXYCHOLIC ACID WITH CHENODEOXYCHOLIC ACIDS

This invention relates to novel compositions and an improved method for dissolving gallstones and/or reducing lipid levels, cholesterol levels and triglyceride levels which comprises orally administering, to one in need of such treatment, an effective amount of chenodeoxycholic acid (CDCA) of the formula:

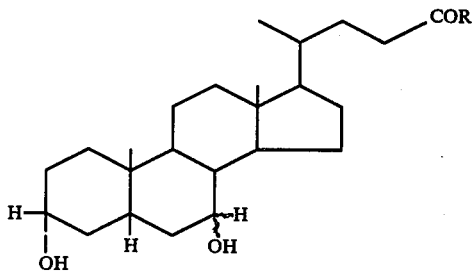

wherein R is —OH, —NHCH$_2$COOH or —NHCH$_2$CH$_2$SO$_3$H; wherein the improvement comprises coadministering an effective amount of hyodeoxycholic acid (HDCA) sufficient to effect safening the administration of Compound I.

CDCA and its pharmacological actions (I, supra) are disclosed in U.S. Pat. No. 3,859,437 which patent is hereby incorporated by reference. See also "Chenodeoxycholic Acid — Therapy of Gallstones", Hofmann and Paumgartner F. K. SCHATTAUER Verlag, New York (1974).

Preferred compounds include 3α, 7α dihydroxy-5β-cholanic acid; 3α, 7β-dihydroxy-5β-cholanic acid and the like. Most preferred is 3α, 7α-dihydroxy-5β-cholanic acid which is the compound utilized for the most satisfactory results.

Pharmacological studies employing rats indicate that the administration of CDCA alone causes slight to mild periportal hepatitis, nuclear enlargement of the hepatocytes and elevations in the blood of serum glutamic-oxaloacetic transaminase (SGOT), serum glutamic pyruvic transaminase (SGPT) and alkaline phosphatase (alk. phos.) indicating liver damage. When HDCA is administered with CDCA to rats either as a physical mixture or as hog bile, there is a reduction in SGOT, SGPT and alkaline phosphatase indicating a safening effect of HDCA. The compositions are generally administered in a ratio of CDCA to HDCA in the range of from about 0.7 to about 2.0 and, preferably in the range of from about 0.8 to about 1.5. It has also been discovered that hog bile, the only bile containing HDCA, may also be administered in a manner similar to the physical mixture to produce an effect similar to the physical mixture. Hog bile generally contains from about 10 to about 50% CDCA and from about 10 to about 50% of HDCA in addition to other bile acids.

The following example illustrates the purification of dessicated hog bile (Wilson).

Purification of Hog Bile

To 3.0 liters of hot methanol is added hog bile powder (500 g.; purchased from Inolex - Lot No. 0108A022). The mixture is brought to boiling for 30 minutes and filtered through a Buchner funnel. The collected solid is added to hot methanol (1.0 l.) and filtered. To the combined filtrates is added barium hydroxide (120 g.) in water (1.0 l.). The precipitate which forms is collected and extracted with hot ethanol (2.0 l.). To the combined methanol and ethanol filtrates, heated to 70° C. is added a solution of zinc sulfate (150 g.). in methanol (500 ml.). The solution is cooled and precipitated barium sulfate removed by filtration. The solvents are removed by evaporation down to a volume of about 1.0 liter. To this is added sodium chloride (100 g.) and ethyl acetate (1.0 l.). The mixture is heated (50°–55° C.) and the pH adjusted to 5.5 with concentrated hydrochloric acid. The ethyl acetate phase is separated from the aqueous phase while hot. The aqueous phase is extracted with fresh ethyl acetate (800 ml.). The ethyl acetate extracts are combined, washed successively with water (4 × 500 ml.), dried over anhydrous sodium sulfate, filtered and the filtrate reduced in volume to 700 ml. The precipitate which forms is collected and dried to afford 141 grams of hog bile acid preparation containing about 25% CDCA and about 40% HDCA.

The following tests and results shown in Tables I and II, (infra), indicate the safening effect of the administration of HDCA together with CDCA whether administered as a physical mixture or as a hog bile mixture.

TEST I

Twenty female Sprague-Dawley rats, weighing 200-300 grams, were divided into four groups of five per group with uniform weight distribution between groups. Each rat was placed in an individual cage. The average daily feed consumption was calculated, following an adjustment period when all rats were fed ground Purina ® lab chow. The test materials were mixed in the diet at the level necessary to provide the dosage listed in Table I.

The rats were weighed weekly and the daily feed consumption calculated from the total weekly intake. The concentration of the test materials in the feed was adjusted at the end of the first week to maintain the proper daily dose levels. Following a 14 day treatment period, all rats were sacrificed. Blood was collected for determination of alk. phos., SGOT and SGPT.

TABLE I

| Compounds | Mg/kg/day | Feed Consumption (grams/day) Week 1 | Week 2 | Change in Body Wt. | Alk. Phos. mu/ml | SGOT mu/ml | SGPT mu/ml |
|---|---|---|---|---|---|---|---|
| Control | — | 17.3 | 16.0 | + 13 g. | 183 ± 22.9 | 66.8 ± 13.4 | 27.6 ± 3.1 |
| CDCA | 600 | 13.0 | 15.9 | − 3 g. | 294 ± 48.9 | 515.4 ± 71.8 | 96.4 ± 11.7 |
| CDCA/HDCA | 600/480 | 15.7 | 15.4 | + 8 g. | 287 ± 19.0 | 162.2 ± 24.3 | 61.4 ± 11.5 |
| Hog Bile Acid Preparation | 300/480 | 17.9 | 17.5 | + 12 g. | 217 ± 13.6 | 52.0 ± 5.2 | 15.8 ± 3.7 |

TEST 2

Ten Long-Evans female rats were divided into two groups of five each. The rats were fed Purina ® lab chow mixed with CDCA or dried hog bile. The dried hog bile contains approximately 25% CDCA and approximately 40% HDCA and was mixed in the feed at four times the concentration as CDCA so that each group of rats would receive approximately 600 mg. CDCA/kg./day. Following a 2 week treatment, the 10 rats plus five control rats were sacrificed and the blood collected for liver enzyme determinations. The following Table II shows the results.

TABLE II

| | Group Means ± SEM | | | | | | |
|---|---|---|---|---|---|---|---|
| | Feed Consumption (gms/da) Week | | | Bodyweights (gms) Week | | CDCA Intake (mg/kg/da) Week | |
| Treatment | 0 | 1 | 2 | 0 | 1 | 1 | 2 |
| CDCA | 18.6 ± 1.0 | 9.9 ± 1.1 | 11.7*** ± 0.9 | 284.6 ± 5.3 | 256.4** ± 10.4 | 391.8 ± 54.2 | 455.8*** ± 31.1 |
| Dried Hog Bile (Inolex Lot | 15.7 ± 1.0 | 11.7 ± 0.8 | 20.6 ± 1.2 | 287.0 ± 3.6 | 287.6 ± 4.7 | 444.0 ± 26.1 | 715.4 ± 33.0 |

**p<0.01 when compared to dried hog bile
***p<0.001 when compared to dried hog bile

TABLE III

| | Blood Chemistry | | |
|---|---|---|---|
| Treatment | SGOT mu/ml | SGPT mu/ml | Alk. Phos. mu/ml |
| Control | 64.8 ± 13.4 | 24.6 ± 4.3 | 154.4 ± 16.6 |
| CDCA | 1021* ±328.2 | 245.0* ± 88.6 | 213.6* ± 16.9 |
| Dried Hog Bile (Inolex Lot No. 0108A022 | 90.4 ± 17.3 | 33.0 ± 1.9 | 199.2 ± 28.9 |

*p<0.05 when compared to controls

The compositions containing either the physical mixture of CDCA (I) and HDCA or dried hog bile itself as the active ingredients and also the physical mixture of CDCA (I) and HDCA or purified hog bile effect a dissolution of gallstones and/or effect a reduction of lipid levels, cholesterol levels or triglyceride levels while causing a lowering of SGOT and SGPT relative to the administration of CDCA itself. The physical mixture or hog bile can be administered in a wide variety of therapeutic dosages in conventional pharmaceutical carriers. For example, by oral administration in the form of a tablet or capsules or oral solutions or suspensions.

The therapeutic compositions comprise the active ingredients in a unit dosage form of from about 40 mg. to about 250 mg. of CDCA and from about 10 mg. to about 250 mg. of HDCA and preferably CDCA in the range of from about 125 mg. to about 250 mg. and HDCA in the range of from about 125 mg. to about 250 mg. The daily dosage of the composition may be varied over a wide range varying from about 50 mg. to about 2 g. of CDCA and from about 10 mg. to about 3.5 g. of HDCA. The product is preferably administered in subdivided doses containing 50, 100, 150, 250 and 500 mg. of the active ingredients for the symptomatic adjustment of the dosage to the patient to be treated. The total daily dosage of the compositions comprising CDCA and HDCA is in the range of from about 250 mg. to about 5.5 g. per day with an average dose containing about 18 mg./kg./day. It should be understood that this invention also embraces the addition of pure CDCA to crude hog bile to adjust the percentage of CDCA in a unit dosage to an effective amount.

The compounds of this invention may be administered in the form of a nontoxic, pharmaceutically acceptable salts, for example, the alkaline metal salts, such as the sodium or potassium salts thereof.

What is claimed is:

1. In a method for dissolving gallstones, reducing lipid levels, cholesterol levels and triglyceride levels which comprises orally administering, to one in need of such treatment, an effective amount of chenodeoxycholic acid (CDCA) of the formula:

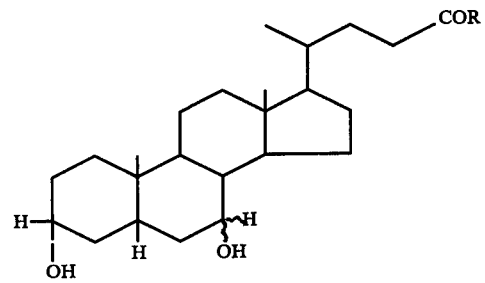

wherein R is —OH, —NHCH$_2$COOH or —NHCH$_2$CH$_2$SO$_3$H, and the nontoxic, pharmaceutically acceptable salts thereof; the improvement comprising coadministering an effective amount of hyodeoxycholic acid (HDCA) sufficient to effect safening the administration of said CDCA, and in a ratio of from about 0.7 of CDCA to about 2.0 of HDCA.

2. The method of claim 1 wherein the composition comprises CDCA and HDCA in the ratio of from about 0.8 to about 1.5.

3. The method of claim 1 wherein the CDCA is 3α,α7-dihydroxy-5-β-cholanic acid.

4. The method of claim 3 wherein the composition comprises 3α, 7α-dihydroxy-5-β-cholanic acid and HDCA and which is administered in a daily dosage of from 50 mg. to 2000 mg. per day of 3α, 7α-dihydroxy-5-β-cholanic acid and a safening amount of HDCA in the range of from 10 mg. to 3,500 mg.

* * * * *

UNITED STATES PATENT AND TRADEMARK OFFICE
CERTIFICATE OF CORRECTION

PATENT NO. : 4,079,133
DATED : March 14, 1978
INVENTOR(S) : David T. Drees & Anthony R. Imondi It is certified that error appears in the above-identified patent and that said Letters Patent are hereby corrected as shown below:

Col. 3, Table II under the heading Treatment " (Inolex Lot " should read -- (Inolex Lot No. 0108A022) --.

Signed and Sealed this

Twenty-seventh Day of June 1978

[SEAL]

Attest:

RUTH C. MASON
Attesting Officer

DONALD W. BANNER
Commissioner of Patents and Trademarks